United States Patent
Wang et al.

(10) Patent No.: US 11,913,063 B2
(45) Date of Patent: *Feb. 27, 2024

(54) SYSTEMS AND METHODS FOR COMBINED DETECTION OF GENETIC ALTERATIONS

(71) Applicant: PREDICINE, Inc., Hayward, CA (US)

(72) Inventors: Xiaohong Wang, Dublin, CA (US); Pan Du, Dublin, CA (US); Shidong Jia, Palo Alto, CA (US)

(73) Assignee: PREDICINE, INC., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/497,230

(22) Filed: Oct. 8, 2021

(65) Prior Publication Data

US 2022/0213527 A1 Jul. 7, 2022

Related U.S. Application Data

(63) Continuation of application No. 16/335,661, filed as application No. PCT/US2017/052832 on Sep. 21, 2017, now Pat. No. 11,174,503, which is a continuation of application No. PCT/US2017/027830, filed on Apr. 16, 2017.

(60) Provisional application No. 62/397,923, filed on Sep. 21, 2016.

(51) Int. Cl.
C12P 19/34 (2006.01)
C12Q 1/6806 (2018.01)

(52) U.S. Cl.
CPC ...... *C12Q 1/6806* (2013.01); *C12Q 2600/112* (2013.01); *C12Q 2600/158* (2013.01)

(58) Field of Classification Search
CPC .................................................... C12Q 1/6869
See application file for complete search history.

(56) References Cited

U.S. PATENT DOCUMENTS

| | | | |
|---|---|---|---|
| 2014/0066317 A1* | 3/2014 | Talasaz | C12N 15/1072 506/2 |
| 2018/0340169 A1* | 11/2018 | Belhocine | C12N 15/1096 |
| 2020/0291454 A1* | 9/2020 | Belhocine | C12Q 1/6806 |

* cited by examiner

*Primary Examiner* — Kenneth R Horlick
(74) *Attorney, Agent, or Firm* — Wilson Sonsini Goodrich & Rosati

(57) ABSTRACT

Disclosed are systems and methods for simultaneous detection of DNA and RNA genetic alterations comprising gene splicing variants, mutations, indel, copy number changes, fusion and combination thereof, in a biofluid sample from the patient without physically separating RNA from DNA. The systems and methods are similarly applicable to the simultaneous detection of DNA and RNA genetic alterations in solid tissues comprising gene splicing variants, mutations, indel, copy number changes, fusion and combination thereof. The present method utilized a barcoding method for analysis. The streamlined methods improve the simplicity, quantification accuracy and detection sensitivity and specificity of non-invasive detections of biomarkers.

29 Claims, 9 Drawing Sheets

Specification includes a Sequence Listing.

SYSTEMS AND METHODS FOR COMBINED DETECTION OF GENETIC ALTERATIONS

CROSS-REFERENCE TO RELATED APPLICATIONS

This application is a continuation of application Ser. No. 16/335,661, filed Mar. 21, 2019 (now U.S. Pat. No. 11,174,503, issued Nov. 16, 2021), which is a National Stage Entry of International Application No. PCT/US2017/052832, filed Sep. 21, 2017, which claims the benefit of U.S. Provisional Application No. 62/397,923, filed Sep. 21, 2016; International Application No. PCT/US2017/052832 is a continuation-in-part of International Application No. PCT/US2017/027830, filed Apr. 16, 2017, each of which is incorporated by reference herein in its entirety.

The instant application contains a Sequence Listing which has been submitted electronically in ASCII format and is hereby incorporated by reference in its entirety. Said ASCII copy, created on Dec. 1, 2021, is named 59987-702_301_SL.txt and is 881 bytes in size.

FIELD OF INVENTION

The invention relates generally to the field of precision medicine, specifically cancer prediction, diagnostics or prognostics, and, more specifically of Gene RADAR (RNA and DNA digital Reading) and NGS methods for detecting cancer mutations in a cancer patient by the simultaneous detection of genetic alterations including RNA splicing variants, DNA- and/or RNA-based mutation, indel, long deletions, copy number variation, gene fusions from solid tissues or biofluid samples, e.g., plasma, serum, urine, and saliva etc.

BACKGROUND

Cancer is one of the leading causes of morbidity and mortality worldwide, with approximately 14 million new cases in 2012. The number of new cases is expected to rise by about 70% over the next 2 decades. The standard treatments of cancer include chemotherapy, irradiation therapy, surgery and more recently immune therapy. Detecting genetic alterations is a key step for cancer diagnosis and personalized medicine, thus genetic alteration screening has the potential to improve the overall healthcare of cancer patients.

Liquid biopsy including blood analysis is especially useful for cancer diagnosis because of the accessibility issue of the tumor and to avoid repetitive tumor biopsy during the course of treatments. Both DNA and RNA carries important genetic variant information for cancer diagnosis. For example, DNA can detect DNA mutations, DNA copy number and structure variations, while RNA can detect gene splicing and fusions, and RNA expression changes and also confirm DNA level mutations if they are expressed at RNA level. Therefore, there is a great need for detection of both DNA and RNA alterations from the same sample. The conventional way to detect both DNA and RNA alterations has to first physically separate RNA from DNA. However, the separation of RNA from DNA can cause material loss for both DNA and RNA, and the separation process is also cost and time consuming. Here we invent a solution of detect both DNA and RNA alterations without needing to physically separate RNA from DNA.

Next generation sequencing (NGS) is accelerating the discovery of genetic alteration in human diseases. One of the major advantage of next generation sequencing is multiplex sequencing. NGS technology also enables adding molecular barcode to identify the source of the NGS reads.

SUMMARY OF THE INVENTION

The present invention provides a method for detecting a genetic alteration from a biofluid comprises: a) obtaining nucleic acids comprising a single strand RNA (ssRNA) and a double strand DNA (dsDNA) from said biofluid; b) labeling ssRNA with a first barcode during reverse transcription step and converting ssRNA to double stranded cDNA wherein the ds-cDNA comprises RNA-specific barcodes, while the unbarcoded dsDNA is in the same tube; and c) labeling the DNA mixture comprising the unbarcoded dsDNA and the barcoded ds-cDNA with a second barcode; and d) analyzing the genetic alteration by a bioinformatics tool by deciphering two-layer RNA molecular barcoding. The present invention comprises a step of sequencing barcoded RNA and DNA simultaneously. The present invention further comprises a step of analyzing RNA and DNA sequencing results for detecting a genetic alteration after the sequencing.

The bioinformatics analysis enables 1) differentiation of the RNA derived reads from DNA derived reads by checking the RNA specific tags in the sequence reads; 2) the suppression of the sequencing and background noise by creating consensus of Next Generation Sequence (NGS) reads from the same original molecules, which is defined based on molecular barcodes and the mapping location of the reads; and 3) accurate quantification of RNA by combining two types of barcodes (RNA molecular barcodes+DNA molecular barcodes), and the quantification of DNA (only using DNA molecular barcodes) at the same time.

The present invention further provides that reverse transcription step of the barcoded ssRNA comprises 1) reverse transcribing ssRNA to cDNA after ssRNA is annealed to an oligonucleotide comprising a RNA specific tag and random molecular barcodes; and 2) converting the cDNA to a ds-cDNA, wherein such barcoding step is named single-sided RNA barcoding.

The present invention further provides that reverse transcription step of the barcoded ssRNA, wherein the converting step of the cDNA to a ds-cDNA further comprising a second oligonucleotide with molecular barcode, wherein such barcoding step is named double-sided RNA barcoding.

In some embodiments, the barcoded DNA mixture is subsequently analyzed by Next Generation Sequencing.

In some embodiments, the genetic alterations to be detected comprising one or more gene splice variants, mutations, indels, long deletions, copy numbers changes, fusions and combination thereof.

The biofluid samples are selected from a group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascetic fluid, tumor cyst fluid, amniotic fluid, and a combination thereof. In preferred embodiments, the nucleic acid sample can be obtained by extracting both DNA and RNA from the biofluid sample simultaneously.

The present invention further comprises the detection of presence and absence of a genetic alteration is indicative of a disease and the disease is one or more cancers, for example, a genetic alteration is from an androgen receptor gene mutation which predicts prostate cancer. Or a genetic alteration is from lung panel gene mutation which predicts lung cancer.

The present invention further provides a platform/system for detecting genetic alterations in a patient, comprising: (a) a kit of reagents for circulating nucleic acid extraction and oligonucleotides targeting one or more gene alterations without separating RNA and DNA in said nucleic acid extraction; and (b) bioinformatics analysis solution to decipher DNA and RNA-derived information.

The system can be a closed system and an automated system.

Disclosed are systems and methods for detecting genetic alterations in lung, breast, ovarian, prostate and other cancer patients. In one aspect, the disclosed method comprises assaying the presence or absence of one or more gene splice variants and additional genetic alterations such as mutation, indels, long deletions, copy number variation, gene fusions etc. in a biofluid sample from the said patient.

The present invention provides a two-layer RNA molecular barcoding method for labeling a nucleic acid sample including a step for RNA molecular barcoding comprising adding a firstRNA specific molecular barcodes, wherein said RNA specific molecular barcodes are incorporated into a ds-cDNA converted from a ssRNA; and a step for DNA molecular barcoding comprising adding a second molecular barcodes by ligation of oligo adaptor to barcoded and unbarcoded dsDNA in said nucleic acid sample for further genetic alteration analysis.

The present invention further provides a system for detecting a genetic alteration of from a biofluid comprises: a) reagents for circulating nucleic acid extraction; b) barcoding sequences for two-layer RNA molecular barcoding; and c) bioinformatics tool to analyzing DNA and RNA-derived information.

In some embodiments, the biofluid sample is a sample of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascetic fluid, tumor cyst fluid, amniotic fluid, or a combination thereof.

In some embodiments, the step of assaying comprises extracting RNA from the biofluid sample and subsequently reverse transcribing the extracted RNA into a complementary DNA.

In other embodiments, the step of assaying comprised extracting both DNA and RNA from the biofluid sample simultaneously and then reverse transcribing the extracted RNA to a complementary DNA.

In some embodiments, the resultant complementary DNA is subsequently measured by Next Generation Sequencing, Polymerase Chain Reaction including qPCR and digital PCR, array-based technologies, and other related technologies.

The present invention further disclosed that Gene RADAR (RNA and DNA single molecular digital Reading) bioinformatics analysis tool can decipher two-layer RNA molecular barcoding to: (1) enable differentiation of the RNA derived reads from DNA derived reads by checking the RNA specific tags in the sequence reads; (2) enable the suppression of the sequencing and PCR errors by creating consensus of NGS reads from the same original molecular (based on molecular barcodes and the mapping location of the reads); (3) enable the quantification of RNA by combining two types of barcodes (RNA molecular barcodes+ DNA molecular barcodes), and the quantification of cfDNA (only using DNA molecular barcodes) at the same time. Because the highly expressed genes need much higher barcode diversity to identify all unique RNA fragments than cfDNA, the two-layer barcode scheme combined with Gene RADAR analysis tool enables simultaneous detection of RNA and DNA genetic alterations from a single sample.

BRIEF DESCRIPTION OF THE DRAWINGS

FIG. 5 discloses SEQ ID NOS 1-2, respectively, in order of appearance.

DETAILED DESCRIPTION OF THE INVENTION

Figure 1:
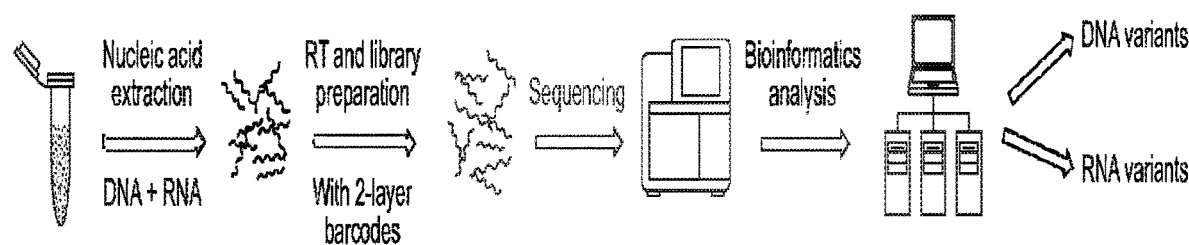
FIG. 1 shows a Gene RADAR (RNA and DNA single molecular digital Reading) assay flowchart depicting the steps from biofluid or tissue to wet lab testing and data analysis of RNA- and DNA-derived genetic alterations.

The present invention provides a method for combined detection of genetic alterations from a biofluid. The present invention also provides a two-layer RNA molecular barcoding method for labeling RNA and DNA in nucleic acids mixture from the biofluid samples for further genetic analysis.

Definitions

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

The term "patient," as used herein preferably refers to a human, but also encompasses other mammals. It is noted that, as used herein, the terms "organism," "individual," "subject," or "patient" are used as synonyms and interchangeably.

The term "genetic alteration" comprise gene splice variants, SNV, Indel, CNV, fusion and combination thereof.

The term circulating tumor DNA (ctDNA) or circulating tumor RNA (ctRNA) is tumor-derived fragmented DNA or RNA in the bloodstream that is not associated with cells. ctDNA or ctRNA should not be confused with cell-free DNA (cfDNA) or cell-free RNA (cfRNA), a broader term which describes DNA or RNA that is freely circulating in the bloodstream, but is not necessarily of tumor origin.

The term "barcoding" or "barcode" means using one or more oligonucleotides as tags/markers to incorporate into a dsDNA. The barcodes will be sequenced together with the unknown sample DNA. After sequencing the reads are sorted by barcode and grouped together (de-multiplexing). Barcode includes molecular barcode and sample barcode.

A "molecular barcode" is a unique multiple-base pair sequence used to identify unique fragments and "de-duplicate" the sequencing reads from a sample. This, along with the random start sites, helps identify and remove PCR duplicates. Molecular barcodes can be used to suppress sequencing and PCR errors, and reduce false positives subsequently. Whereas sample barcodes, also called indexed adaptors, are customarily used in most current NGS workflows and allow the mixing of samples prior to sequencing.

The term "RNA molecular barcoding" means incorporating barcodes during the process of reverse transcription of RNA and dsDNA library preparation. RNA molecular barcoding can incorporate a molecular barcode or multiple molecular barcodes. A RNA specific barcode can be a RNA specific tag, a molecular barcode, a sample barcode or a combination.

The term "DNA barcoding" means barcoding at dsDNA level with a multiple-base pair sequence that is part of the adapter for multiplex sequencing. In some embodiment, the adapter is designed in house. The incorporated DNA barcodes can be molecular barcodes alone or both molecular barcodes and sample barcodes.

The term "positive" strand also known as the "sense" strand or coding strand, is the segment within double-stranded DNA that runs from 5' to 3'. The term "negative" strand also known as the "anti-sense" stand of DNA is the segment within double-stranded DNA that runs from 3' to 5'.

The term "bioinformatics" means a sequencing analysis tool/software including but are not limited to Gene-RADAR software or any software that can analyze DNA/RNA sequencing results.

The present invention provides a method for barcoding an oligonucleotide tag on the RNA sample during reserve transcribing it to cDNA and ds-cDNA, wherein the reverse transcription step of the ssRNA includes 1) reverse transcribing ssRNA to cDNA using a gene-specific or random primer annealed to an oligonucleotide comprising a RNA specific tag and random molecular barcodes; and/or 2) converting the cDNA to a ds-cDNA. In some embodiments, converting the cDNA to a ds-cDNA is conducted by annealing a non-coded primer, wherein such barcoding step is named single-sided RNA barcoding. In one embodiment, the RNA specific tag comprising an oligo nucleotide. The random molecular barcodes comprise another oligonucleotide. The oligo nucleotide consists of 5, 8, 10, 12, 14, 15, 20 nucleic acid bases. In another embodiment, the oligo nucleotide can be designed for fitting the identification in further analysis.

In some other embodiments, the converting step of the cDNA to a ds-cDNA is conducted by annealing an oligo-nucleotide comprising a second RNA specific molecular barcode, wherein such barcoding step is named double-sided RNA barcoding. In some embodiment, the first and second RNA specific molecular barcode is the same; in some other embodiment, the first RNA and second RNA specific molecular barcode is not the same.

In preferred embodiments, the genetic alterations include gene splice variants, mutations, indels, long deletions, copy number changes, fusions and combination thereof. The method of detecting the alterations is used to detect the changes of above.

Figure 7A:
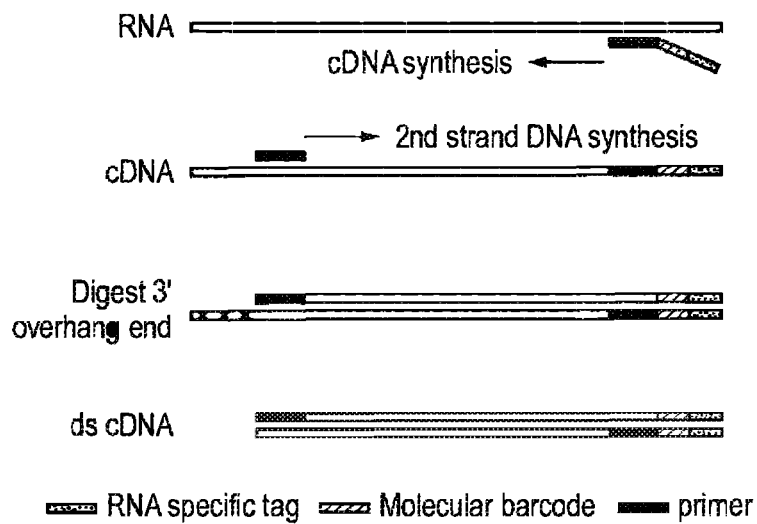
FIGS. 7A-7C show embodiments of two-layer RNA+ DNA molecular barcoding scheme. (A) RT with single-side barcodes; (B) RT with double-side barcodes; (C) Ligate barcoded adapters to double stranded DNA
Figure 7B:
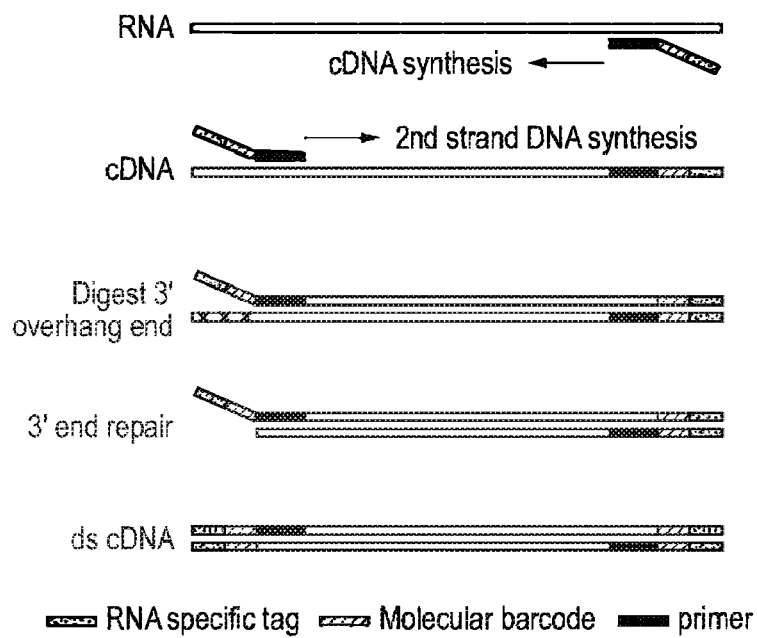
Figure 7C:
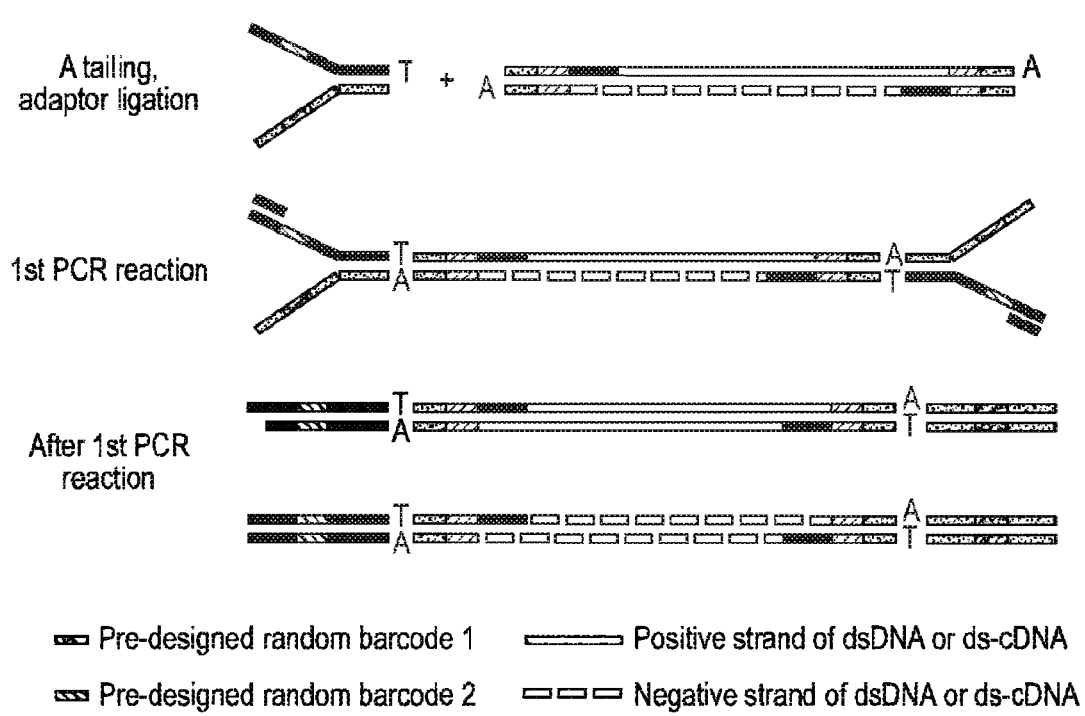
Figure 8:
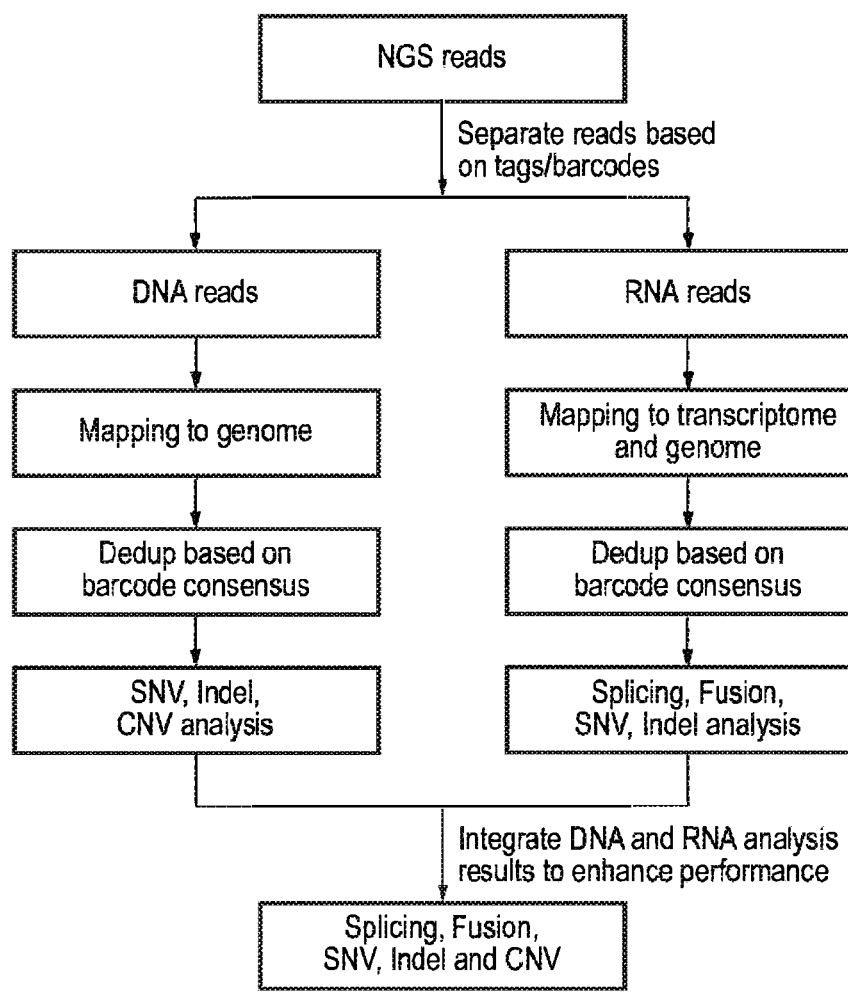
FIG. 8 shows the Gene RADAR Bioinformatics analysis workflow.

The present invention further disclosed a two-layer RNA molecular barcoding scheme for further genetic analysis to distinguish RNA and DNA derived signals. Two-layer RNA molecular barcoding can reduce the background noise and variants (FIG. 2) after barcode consensus noise suppression. In preferred embodiments, the first layer RNA molecular barcoding scheme includes adding RNA specific tags plus random molecular barcodes, as shown in FIG. 7A and FIG. 7B. FIG. 7A shows the procedure of adding single-sided RNA molecular barcodes and converting the single stranded RNA fragment to double stranded cDNA. FIG. 7B shows the procedure of adding double-sided RNA molecular barcodes. Comparing with single-sided molecular barcoding scheme, an additional 3' end repair step is added to get the 3' molecular barcodes. After RNA is converted as ds-cDNA (double-stranded cDNA), it will be treated the same as regular ds-cfDNA. Then the DNA level barcodes are added by ligation of adaptors, as shown in FIG. 7C.

In one embodiment, the barcoded signals from RNA and DNA are read by next generation sequencing, not polymerase chain reaction. Separation of RNA and DNA derived reads is conducted with a bioinformatics analysis tool Gene-RADAR without physically separating nucleic acid extraction into RNA and DNA samples. Therefore, there is no material loss of DNA or RNA due to the physical separation of RNA from DNA. This method also reduced the cost and processing time.

In another embodiment, after the next generation sequencing simultaneous reads signals from RNA and DNA, a database file of the RNA molecular barcodes and DNA molecular barcodes will be utilized to recognize the reads from RNA or DNA with barcode matches. Then the recognized DNA reads are mapped to genome, while the recognized RNA reads are mapped to transcriptome and genome. Barcode consensus are created by merging NGS reads originally from the same molecule (identified based on molecular barcodes and genome mapping location of the reads). The sequencing and PCR errors can be corrected or marked when there are inconsistent variants originally from the same molecule. In some embodiments, the genetic alteration of DNA includes SNV, Indel, long deletion, CNV and DNA fusion. In some embodiments, the genetic alteration of RNA includes splicing, fusion, SNV, Indel analysis. Then the DNA and RNA analysis results are integrated to achieve comprehensive reporting of genetic alterations.

In one embodiment, barcode or barcoding with random oligonucleotide sequences such as 5, 8, 10 12, 14, 15 nucleotides to uniquely tag individual target DNA molecules can be used. In another embodiment, the align nucleotide can be designed for fitting the identification in further analysis. Such application increases the sensitivity and reduce false positives. For example, it can be used for PCR or NGS analysis to identify individual molecules (DNA or RNA fragments) in samples.

In some embodiments, the Gene RADAR detects DNA copy number gains while measuring other RNA level variants including splicing, fusion, SNV, Indel at the same time from the patient biofluid sample.

Present invention further provides a platform for detecting multiple gene variants in a patient, including: (a) a kit of reagents for circulating nucleic acid extraction; (b) barcoding sequences for two-layer RNA+DNA molecular barcoding; and (c) bioinformatics tool to analyzing DNA and RNA-derived information.

The system can be an opened or closed system. And both systems can be automated system. The system can be in a device setting.

In preferred embodiments, the detection of presence and absence of a genetic alteration is indicative of a disease and the disease is one or more cancers. In some other embodiments, presence and absence of multiple genetic alteration is indicative of a disease and the disease is one or more cancers. In some embodiments, genetic alteration detection is lung cancer or prostate cancer oncogene variation.

In one embodiment, the samples include but are not limited to blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, and a combination thereof.

In one aspect, the disclosed method also allows for the reverse transcribed RNA (cDNA) to be included in the mainstream cfDNA library preparation and target enrichment protocol thereby allowing consolidated result of both DNA and RNA from a single biofluid sample. For example, cfDNA and cfRNA are extracted simultaneously, and then the extracted sample are used for reverse transcription and further used for the library processing and sequencing. In the process, there is no need to separate cfRNA from the cfDNA in the biofluid nucleic acid extraction. In some instance, to distinguish the DNA- and RNA-derived signals, the extracted RNA is barcoded with a one-sided or two-sided barcoding method and reverse transcribed in a single step before the steps of library preparation and sequencing.

In some embodiments, the detected genetic alteration information can be used to detect castration resistant prostate cancer in a patient comprising assaying the presence or absence of one or more types of genetic alterations at both RNA and DNA levels, such as androgen receptor gene RNA splice variants (AR-Vs) and RNA/DNA-based mutation detection in a biofluid sample from the patient; wherein the presence of such genetic alterations indicates the presence of the castration resistant prostate cancer in the patient.

In some embodiments, RNA is extracted together with DNAs from circulating nucleic acid and nucleic acid-containing extracellular vesicles in a biofluid sample. No extra step of RNA purification is needed and therefore the process is simplified.

In some embodiments, the sources of nucleic acids are extracellular vesicles (EVs), including exosomes and microvesicles, which have been shown to carry a variety of biomacromolecules including mRNA, microRNA and other non-coding RNAs and considered to be a minimally invasive novel source of materials for molecular diagnostics. See Jia et al., "Emerging technologies in extracellular vesicle-based molecular diagnostics", Expert Rev. Mol. Diagn. 1-15 (2014). EVs are membranous, cell-derived, mixed populations of vesicles, ranging from approximately 40-5000 nm in diameter, which are released by a variety of cells into the intercellular microenvironment and various extracellular biofluids. Methods for procuring a microvesicle fraction from a biofluid sample are described in scientific publications and patent applications (Chen et al., 2010; Miranda et al., 2010; Skog et al., 2008). See also WO 2009/100029, WO 2011009104, WO 2011031892, and WO 2011031877. For example, methods of microvesicle procurement by differential centrifugation are described in a paper by Raposo et al. (Raposo et al., 1996), a paper by Skog et al. (Skog et al., 2008) and a paper by Nilsson et. al. (Nilsson et al., 2009). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel-Taylor (Taylor and Gercel-Taylor, 2008). A method of nanomembrane ultrafiltration concentration is described in a paper by Cheruvanky et al. (Cheruvanky et al., 2007). Further, microvesicles can be identified and isolated from a subject's bodily fluid by a microchip technology that uses a microfluidic platform to separate tumor-derived microvesicles (Chen et al., 2010)

Methods for nucleic acid extraction are generally based on procedures well-known in the art plus proprietary procedures developed in-house. Persons of skill will select a particular extraction procedure as appropriate for the particular biological sample. Examples of extraction procedures are provided in patent publications WO/2009/100029, US 20100196426, US 20110003704, US 20110053157, WO 2011009104, WO 2011031892, US20130131194 and US20110151460. Each of the foregoing references is incorporated by reference herein for its teaching of these methods.

Many biofluids contain circulating nucleic acids and/or nucleic acid-containing EVs. Examples of these biofluids include blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, or a combination thereof.

In some embodiments, the biofluid sample is obtained from a subject who has been diagnosed with cancer based on tissue or liquid biopsy and/or surgery or clinical grounds.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

EXAMPLES

Figure 2:
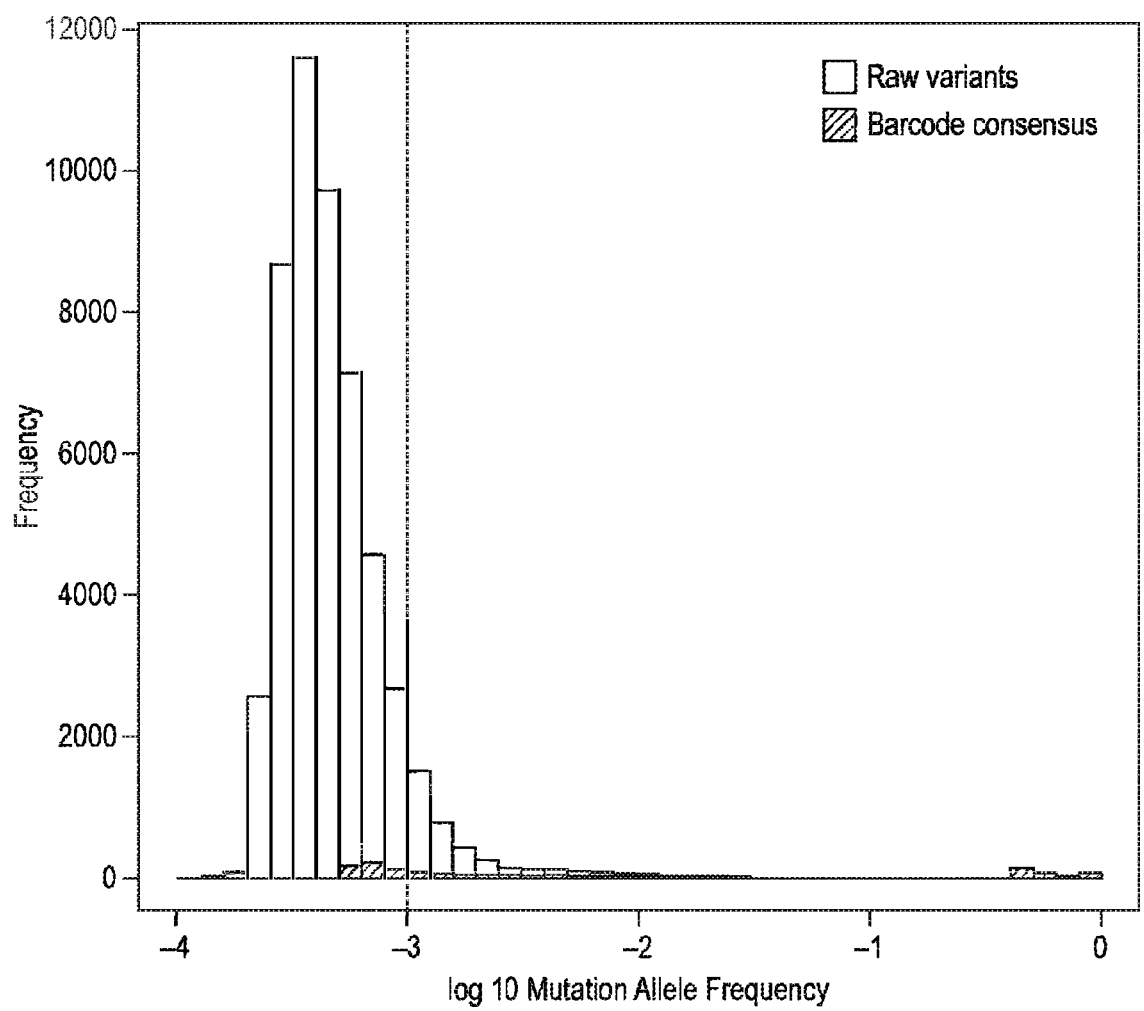
FIG. 2 shows variant allele frequency analysis before and after barcode consensus noise suppression.

Example 1: Variant Allele Frequency Before and After Barcode Consensus Noise Suppression To compare the performance of Gene RADAR and traditional next-generation sequencing using Picard deduplication, which lacks a consensus calling feature, 1.25 ng Horizon reference HD701 was spiked in to normal cfDNA to get 30 ng mixed DNA as input for PrediSeq-Pan Cancer assay. Results from Gene RADAR's analysis pipeline and traditional method were compared and are shown in FIG. 2. Using the traditional method, there were 50,820 identified variants (3,838 variants with variant frequency >0.1%). After applying Gene RADAR's consensus error correction, only 1,104 variants were identified (642 variants with variant frequency >0.1%). This indicates that Gene RADAR's consensus error correction reduces background noise by 97.8% (or 85.1% for variants with AF>0.1%). It was demonstrated that Gene RADAR's error suppression feature enables ultra-high quality sequencing of each input molecule of cfDNA.

Example 2: ctDNA Detection Analysis Sensitivity and Accuracy

Figure 3:
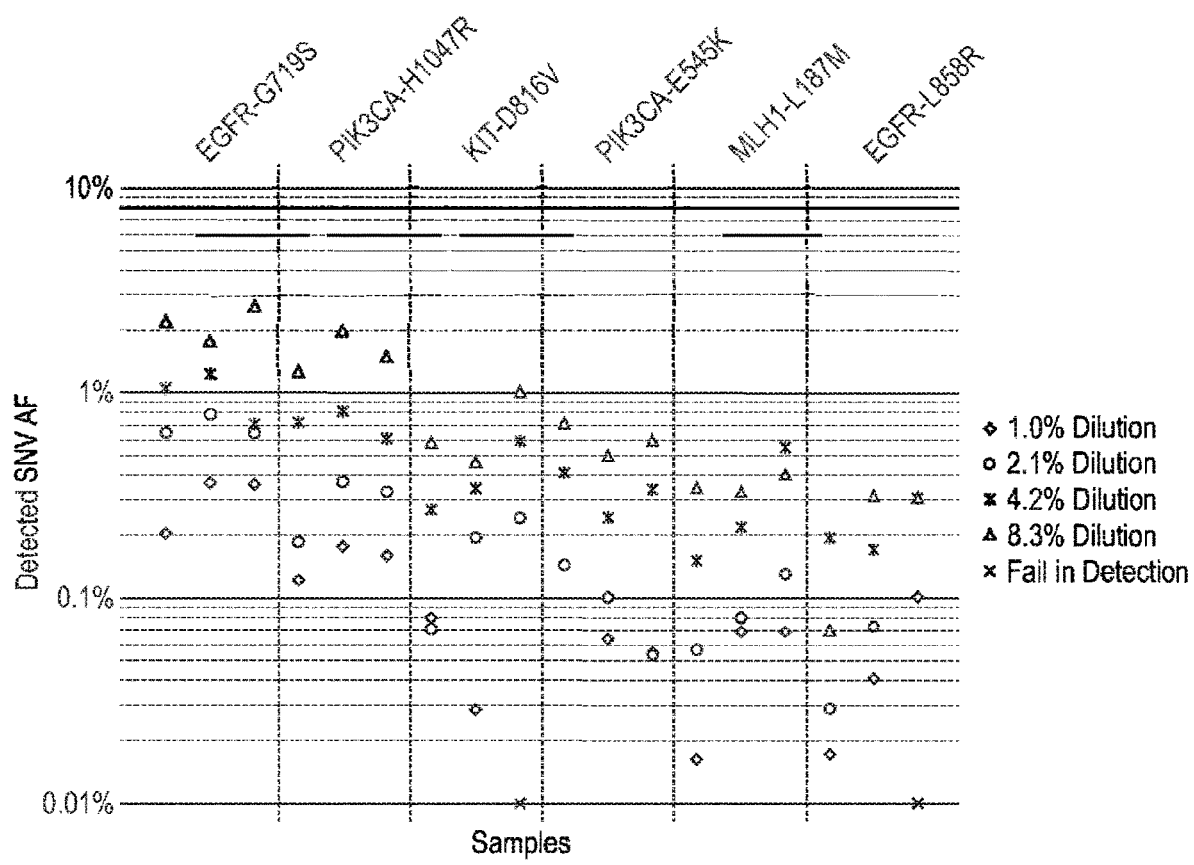
FIG. 3 shows ctDNA detection sensitivity and accuracy analysis.
Figure 4:
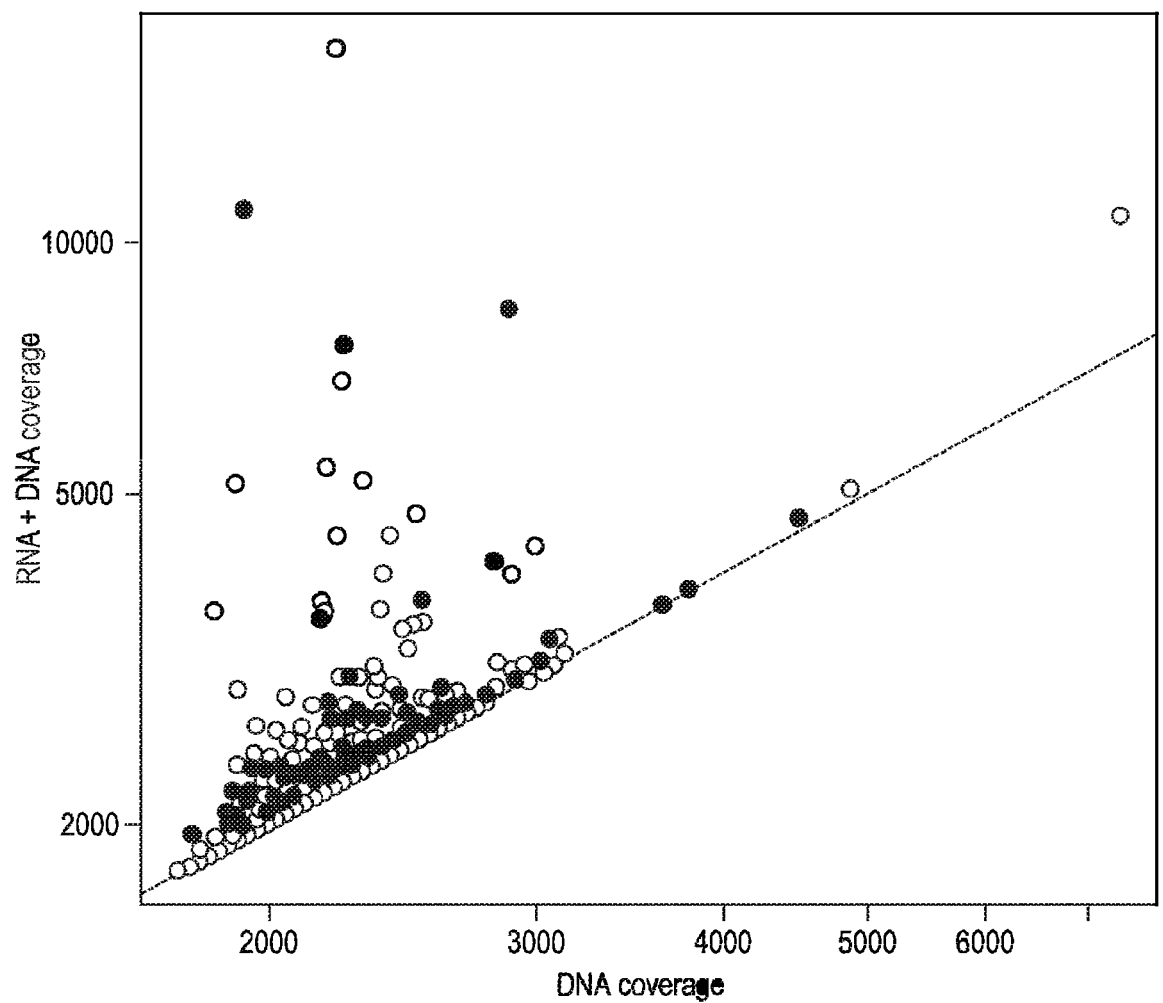
FIG. 4 shows "RNA+DNA" combined detection has better coverage than cfDNA-based detection alone.

To evaluate analytic sensitivity of the PrediSeq-Pan Cancer assay, spike-in of Horizon reference DNA (HD701) was used, and 6 different SNVs were chosen for analysis. Four serial dilution ratios at 8.3%, 4.2%, 2.1%, 1.0% were used in triplicate samples to make a total 72 SNV targets. The SNV allele frequency at which >90% (18 of 20) of SNVs are detected is defined as the limit of detection, and it was calculated at 0.1% based on the data (FIG. 3). To assess the analytical accuracy of the assay's SNV AF detection, we analyzed this same set of data, choosing the SNVs with detected AF>0.1% and calculated the correlation between detected and expected AF, at 0.938.

Example 3

"RNA±DNA" combined detection has better coverage than cfDNA detection alone and additional Sensitivity and Accuracy contributed by cfRNA utilization. Gene RADAR technology utilizes cfDNA and cfRNA from the same sample simultaneously, which adds additional sequencing coverage compared to cfDNA sequencing alone. For the proof of concept study, prostate cancer DNA and RNA was extracted and sequenced from Vcap cell line supernatant. The coverage differences of selected cancer related target genes in DNA only vs. DNA+RNA are presented in FIG. 3. The black dots represent the genes which have matched DNA and RNA level variants. Roughly 17.5% of genes in the selected panel benefits from at least 10% coverage, and thus higher sensitivity contributed by the cfRNA input. In additional, 46.9% of the mutations detected from cfDNA were also detected in the same location from cfRNA (supported by at least 3 reads with target mutation). Therefore, by combining DNA and RNA, additional read coverage and higher confidence variant calls can be obtained over traditional DNA only assays.

Example 4

Figure 5:
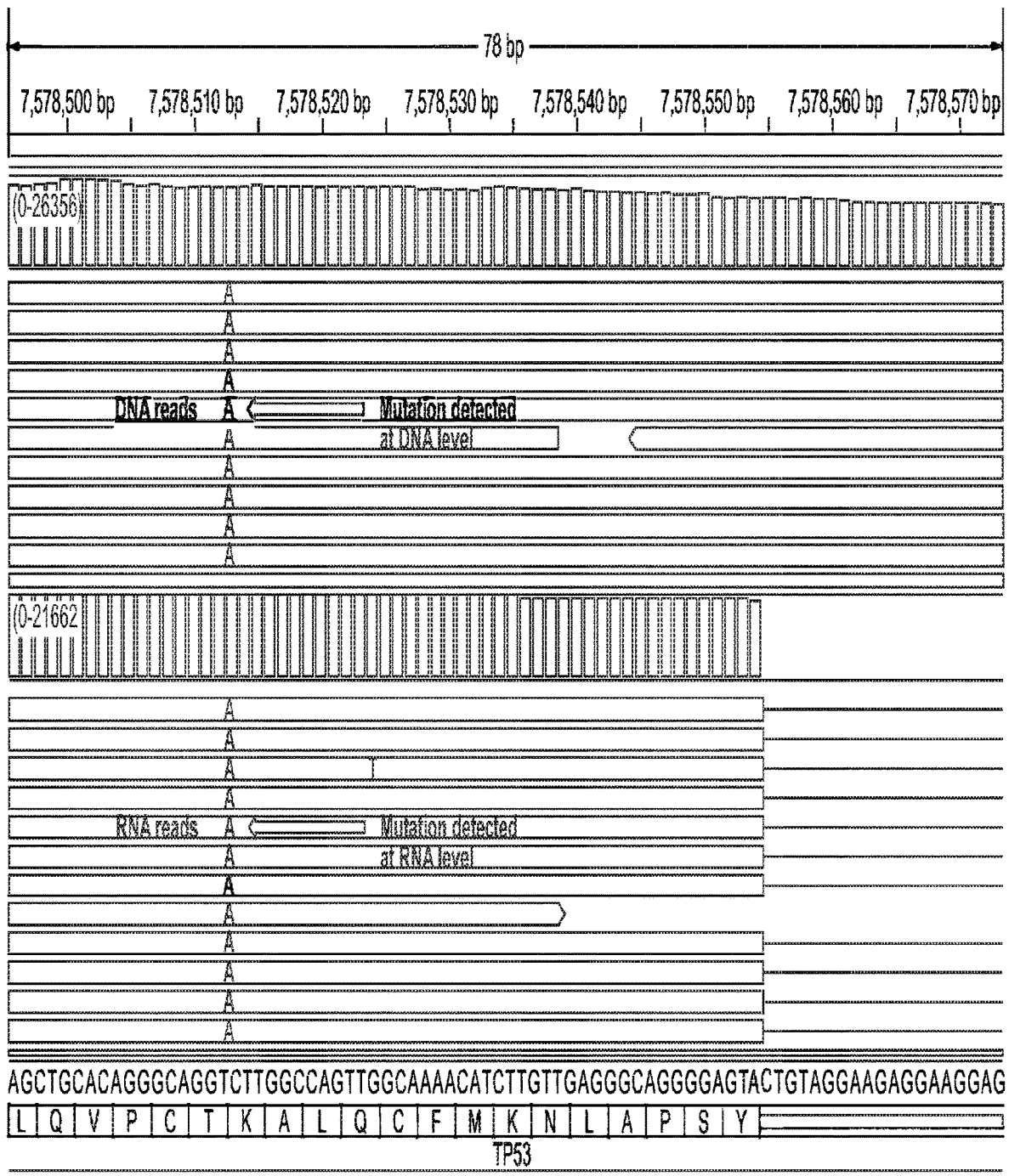
FIG. 5 shows a mutation detected at both DNA and RNA level in a clinic plasma sample.

As shown in FIG. 5, the same TP53:K139N mutation was detected at both DNA and RNA levels from a patient plasma sample using gene RADAR technology.

Example 5

Figure 6:
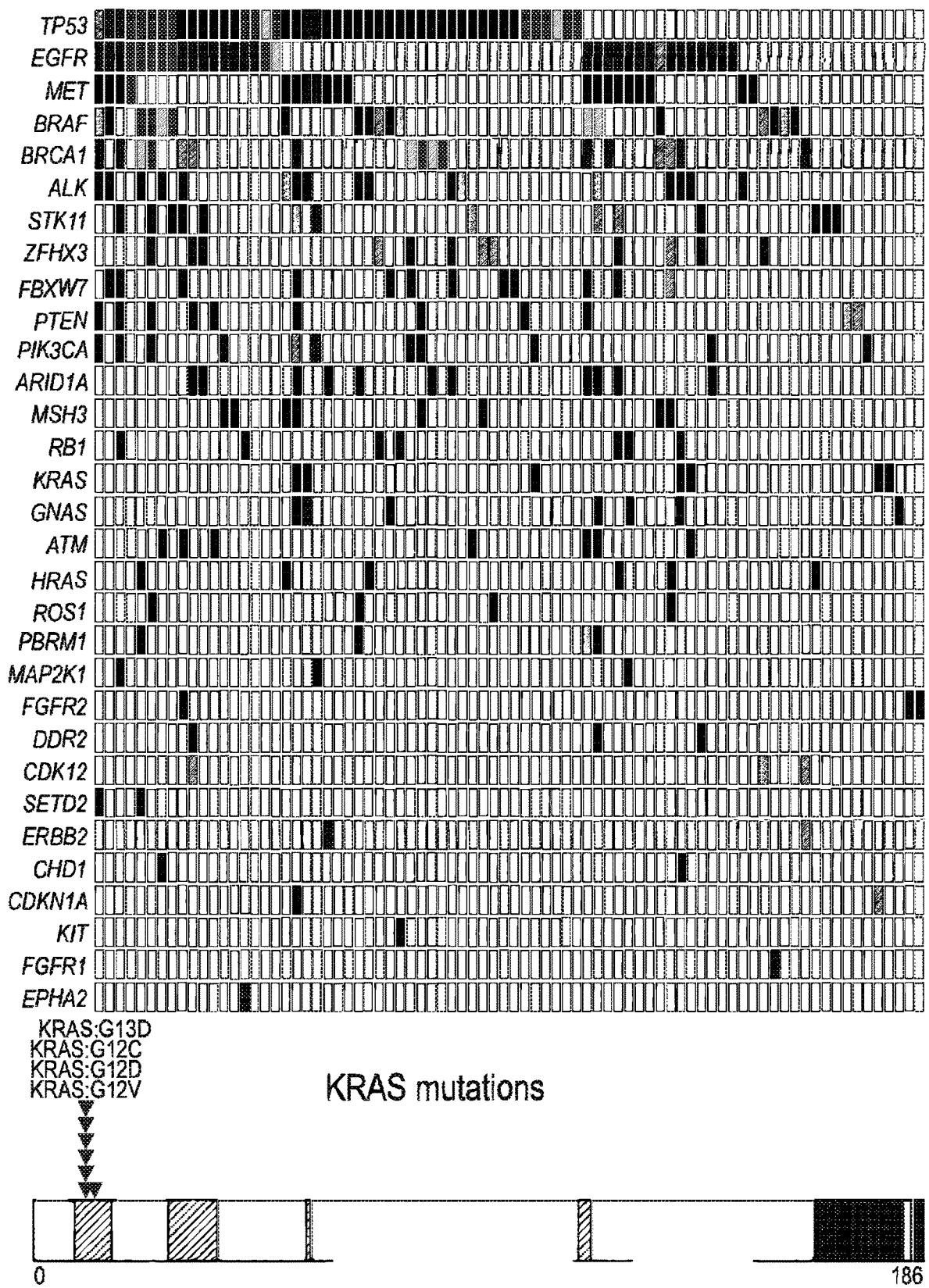
FIG. 6 shows mutation landscape from the clinical samples. All marked mutation represent change in the protein sequences and function.

DNA mutation profiles were identified from 80 lung cancer patient plasma samples using gene RADAR technology. Result is shown in FIG. 6. The top figure shows the mutation overview heatmap, in which each row represents a gene and each column represents a patient plasma sample. The dark color represents there is one or more mutations in the gene (row) for that sample (column). The bottom figure shows the hotspot mutation of KRAS gene.

Example 6

Detection of reverse transcribed AR-Vs in cfDNA and cfRNA extracted from a biofluid sample. This example partly illustrates one embodiment of the disclosed method of detecting AR-V7 and AR-FL in castration-resistant prostate cancer patients.

Circulating nucleic acid is extracted from blood plasma samples using optimized nucleic acid extraction procedure. RNA in the above extraction is then reverse transcribed into cDNA. Two-layer RNA molecular barcoding scheme. In order to quantify the individual RNA molecules, we used two-layer RNA molecular barcoding scheme, as shown in FIG. 7A-7C The first layer RNA molecular barcoding scheme includes adding RNA specific tags plus random molecular barcodes. After cDNA is converted as dsDNA (double-stranded DNA), it was the same as regular ds cfDNA. We then added the DNA level barcodes by ligation of adaptors.

For reverse transcription step, cDNA Synthesis Mix is prepared by adding sequentially 10×RT buffer, MgCl2, DTT, RNaseOUT, and SuperScript® III Reverse Transcriptase. The reverse transcription reaction was performed on thermocycler, then heat inactivated. Then RNA was removed. The cDNA synthesis reaction can be stored at −30° C. to −10° C.

To make the second strand from the cDNA, the following reagents are added to a 0.2-mL tube with 1st strand cDNA from above, DNA polymerase and AR specific primers (contain molecular barcode information). The second strand synthesis reaction is performed as follows: 37° C. for 60 min. The reaction is then cleaned up using a 2× AMPure XP beads according to the manufacturer's instructions. Quantification of DNA sample is performed using Qubit dsDNA High Sensitivity Assay kit and the DNA size distribution is analyzed using Agilent High Sensitivity DNA chips.

cfDNA fragments were subsequently used in PCR test or converted to NGS digital sequence libraries according to the commercial kit manufacturer's instructions with modification. Briefly, DNA was processed to end repaired, 5'-phosphorylated, and 3'-dA-tailed dsDNA fragments. Then DNA fragments were ligated to dsDNA adapters with 3'-dTMP overhangs. The adapters contain sample/molecular barcode information. The libraries were amplified, quantified, and then pooled together. The pooled libraries then subsequently enriched for target genes using biotinylated custom baits of DNA probes and IDT xGen lockdown reagents (IDT) according to the manufacturer's instructions with modification. Quantification of enriched libraries was performed using Qubit dsDNA High Sensitivity Assay kit and the DNA size distribution was analyzed using Agilent High Sensitivity DNA chips. Certain number of enriched libraries were denatured, diluted and loaded on NextSeq 500 (Illumina) for sequencing.

The result shows that AR-V7 junction reads were detected in 6 out of 7 samples. And no AR-V7 junction reads were detected in an AR-V7 negative control sample, and high level of AR-V7 junction reads was detected in the AR-V7 positive control sample (Vcap cell line).

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

We claim:

1. A method comprising:
   (a) providing a first mixture comprising a single-stranded ribonucleic acid (ssRNA) and a double-stranded deoxyribonucleic acid (ds-DNA);
   (b) reverse transcribing the ssRNA in the first mixture, wherein the reverse transcribing comprises labeling the ssRNA with a first molecular barcode to produce a barcoded double-stranded complementary DNA (ds-cDNA), thereby obtaining a second mixture comprising the ds-DNA and the barcoded ds-cDNA; and
   (c) bringing the second mixture or derivative thereof in contact with a plurality of adaptors comprising a second molecular barcode, to couple adaptors of the plurality of adaptors to the ds-DNA and the barcoded ds-cDNA.

2. The method of claim 1, wherein (b) further comprises annealing the ssRNA to an oligonucleotide comprising an RNA-specific tag and a molecular barcode from a set of molecular barcodes; reverse transcribing the ssRNA into a single-stranded cDNA; and converting the single-stranded cDNA into a ds-cDNA.

3. The method of claim 2, wherein converting the single-stranded cDNA into the ds-cDNA further comprises annealing with a second oligonucleotide comprising a second molecular barcode from a set of molecular barcodes.

4. The method of claim 1, further comprising sequencing the ds-DNA and the barcoded ds-cDNA or derivatives thereof to produce a plurality of sequence reads, wherein each of the plurality of sequence reads is associated with at least one of the first molecular barcode and the second molecular barcode.

5. The method of claim 4, wherein (a) further comprises obtaining the first mixture from a biofluid.

6. The method of claim 5, wherein the biofluid is selected from the group consisting of blood, plasma, serum, urine, sputum, spinal fluid, cerebrospinal fluid, pleural fluid, nipple aspirates, lymph fluid, respiratory tract fluid, intestinal tract fluid, genitourinary tract fluid, tear fluid, saliva, breast milk, semen, intra-organ system fluid, ascitic fluid, tumor cyst fluid, amniotic fluid, and a combination thereof.

7. The method of claim 6, wherein the biofluid is a cell-free sample.

8. The method of claim 7, wherein the cell-free sample is plasma.

9. The method of claim 7, wherein the cell-free sample comprises cell-free DNA and cell-free RNA.

10. The method of claim 6, wherein the biofluid is urine.

11. The method of claim 5, further comprising detecting a presence or an absence of a genetic alteration in the biofluid based at least in part on an analysis of the plurality of sequence reads and associated molecular barcodes.

12. The method of claim 11, wherein the genetic alteration is selected from the group consisting of a single nucleotide variant (SNV), a gene splice variant, a mutation, an insertion or deletion (indel), a long deletion, a copy number change, a fusion, and a combination thereof.

13. The method of claim 12, wherein the genetic alteration comprises an SNV.

14. The method of claim 11, wherein the biofluid is obtained or derived from a subject, and wherein the detected presence or absence of the genetic alteration is indicative of a presence or an absence of a disease of the subject.

15. The method of claim 14, wherein the disease comprises a cancer, and wherein the genetic alteration occurs in a cancer-associated gene.

16. The method of claim 15, wherein the disease comprises lung cancer, and wherein the cancer-associated gene is associated with lung cancer.

17. The method of claim 15, wherein the disease comprises prostate cancer, and wherein the cancer-associated gene is associated with prostate cancer.

18. The method of claim 15, further comprising administering a chemotherapy, a radiation therapy, a surgery, or an immune therapy to the subject to treat the cancer of the subject.

19. The method of claim 11, further comprising identifying a plurality of RNA-derived sequence reads and a plurality of DNA-derived sequence reads from among the plurality of sequence reads, and analyzing the plurality of RNA-derived sequence reads and the plurality of DNA-derived sequence reads to detect the presence or the absence of the genetic alteration.

20. The method of claim 19, further comprising detecting a presence or an absence of an RNA genetic alteration from the plurality of RNA-derived sequence reads and a presence or an absence of a DNA genetic alteration from the plurality of DNA-derived sequence reads.

21. The method of claim 20, wherein the RNA genetic alteration comprises an androgen receptor gene RNA splice variant (AR-V).

22. The method of claim 21, wherein the AR-V is AR-V7.

23. The method of claim 4, further comprising mapping the plurality of sequence reads to a reference, thereby producing a plurality of mapped sequence reads.

24. The method of claim 23, further comprising analyzing the plurality of mapped sequence reads to produce a set of consensus sequences corresponding to a same original DNA or RNA molecule, based at least in part on molecular barcodes associated with the plurality of mapped sequence reads.

25. The method of claim 24, wherein analyzing the plurality of mapped sequence reads to produce the set of consensus sequences is based at least in part on mapping locations of the plurality of mapped sequence reads.

26. The method of claim 24, wherein analyzing the plurality of mapped sequence reads to produce the set of consensus sequences further comprises suppressing errors derived from sequencing or polymerase chain reaction (PCR).

27. The method of claim 5, wherein (a) further comprises extracting both DNA molecules and RNA molecules from the biofluid simultaneously.

28. The method of claim 1, further comprising amplifying the ds-DNA and the barcoded ds-cDNA or derivatives thereof.

29. The method of claim 1, further comprising enriching the ds-DNA and the barcoded ds-cDNA or derivatives thereof for a target gene.

* * * * *

SEQUENCE LISTING

<160> NUMBER OF SEQ ID NOS: 2

<210> SEQ ID NO 1
<211> LENGTH: 78
<212> TYPE: DNA
<213> ORGANISM: Homo sapiens

<400> SEQUENCE: 1
agctgcacag ggcaggtctt ggccagttgg caaaacatct tgttgagggc aggggagtac    60
tgtaggaaga ggaaggag                                                 78

<210> SEQ ID NO 2
<211> LENGTH: 20
<212> TYPE: PRT
<213> ORGANISM: Homo sapiens

<400> SEQUENCE: 2

Leu Gln Val Pro Cys Thr Lys Ala Leu Gln Cys Phe Met Lys Asn Leu
1               5                   10                  15

Ala Pro Ser Tyr
            20